US006339104B1

(12) United States Patent
Nishiguchi et al.

(10) Patent No.: US 6,339,104 B1
(45) Date of Patent: Jan. 15, 2002

(54) THERAPEUTIC AGENT FOR PRIMARY BILIARY CIRRHOSIS

(75) Inventors: Shuhei Nishiguchi, Osaka; Ichirou Sounaka, Kawasaki, both of (JP)

(73) Assignees: The City of Osaka, Osaka; Ajinomoto Co., Inc., Tokyo, both of (JP)

( * ) Notice: Subject to any disclaimer, the term of this patent is extended or adjusted under 35 U.S.C. 154(b) by 0 days.

(21) Appl. No.: 09/688,339

(22) Filed: Oct. 16, 2000

Related U.S. Application Data

(63) Continuation of application No. PCT/JP99/02012, filed on Apr. 15, 1999.

(30) Foreign Application Priority Data

Apr. 16, 1998 (JP) ............................................ 10-105274

(51) Int. Cl.[7] ............................................ A61K 31/195
(52) U.S. Cl. ...................................... 514/561; 514/880
(58) Field of Search .................................. 514/561, 838

(56) References Cited

FOREIGN PATENT DOCUMENTS

| JP | 63-54320 | 8/1988 |
|---|---|---|
| JP | 5-229940 | 7/1993 |
| JP | 5-213746 | 8/1993 |
| JP | 5-221858 | 8/1993 |
| WO | 99/53914 | 10/1999 |

OTHER PUBLICATIONS

Marsha Y Morgan et al, "Plasma Amino–Acid Patterns in Liver Disease", GUT, vol. 23, p. 362–370, 1982.

*Primary Examiner*—Rebecca Cook
(74) *Attorney, Agent, or Firm*—Oblon, Spivak, McClelland, Maier & Neustadt, P.C.

(57) ABSTRACT

Disclosed is a therapeutic agent for primary biliary cirrhosis, which contains L-alanine or a pharmaceutically acceptable salt thereof as the active ingredient. The effect of this therapeutic agent is to reduce serum total bilirubin and transaminase value, thereby effectively curing primary biliary cirrhosis. This therapeutic agent can be chronically administrated for a long period of time and exhibits an effect superior to that obtained in ordinary medical therapy.

7 Claims, 1 Drawing Sheet

THERAPEUTIC AGENT FOR PRIMARY BILIARY CIRRHOSIS

This application is a Continuation of international PCT application PCT/JP99/02012, filed Apr. 15, 1999.

FIELD OF THE INVENTION

The present invention relates to a therapeutic agent for primary biliary cirrhosis.

DESCRIPTION OF THE BACKGROUND

Primary biliary cirrhosis is a liver disease of unknown etiology of middle-aged women, which slowly advances and has, as a background, immunologic abnormality and chief complaints of fatigue, pruritus, jaundice, etc. Primary biliary cirrhosis is an intractable disease different from other diseases in both pathology and method of treatment. Concretely, alcohol-induced liver disease is caused by the intake of alcoholic drinks, and abstinence from alcoholic drinks is the primary selective treatment. The action of alanine contained in "antagonistic composition alcohol-induced hepatopathy" which will be described below is to accelerate the alcohol catabolism. Hepatitis, which is not induced by alcoholic drinks, is caused by virus of type A, B or C or by the intake of a large amount of a medicine or the intake of the medicine for a long period of time. For the treatment of hepatitis of such a type, interferon therapy is employed or strong Neo-Minophagen C is used for the treatment. The action of alanine contained in "therapeutic agents for hepatitis" which will be cited below is to inhibit the increase of transaminase by improving the mitochondria function. When these alcohol-induced hepatopathy and hepatitis become chronic, they develop into liver cirrhosis. As for the therapy for liver cirrhosis, only symptomatic therapy for hepatic encephalopathy, hypoalbuminemia and hemorrhage of digestive tracts is possible. However, no therapeutic method for curing liver cirrhosis itself or for inhibiting the advance thereof was developed and, as for alanine, its therapeutic effect on liver cirrhosis is unknown yet.

On the other hand, primary biliary cirrhosis is a liver cirrhosis caused by cholestasis of unknown origin. After the outbreak of the disease, its progress is relatively slow. However, in many of the cases where the symptoms have already been shown, the disease reaches liver cirrhosis in 4 years and the patients die of hepatic insufficiency in about 5 years on average. Patients with primary biliary cirrhosis are thus not convalescing satisfactorily. Although ursodeoxycholic acid is used as the first selective medicine in the treatment of primary biliary cirrhosis, the therapeutic effect thereof is weakened as the conditions of the patients advance. In those advanced stages of diseases, cases in which the symptoms became more serious by the administration of ursodeoxycholic acid were reported. Further, because this disease surely progresses into hepatic insufficiency, patients having the terminal symptoms are obliged to rely on liver transplantation. However, the transplantation has problems such as insufficiency of the organs. Under these circumstances, the development of a medical drug therapy capable of controlling the symptoms and delaying the advance of the disease is demanded. Although it was known to use alanine alone or in combination with other amino acids for preparing a composition for treating patients suffering from alcohol-induced disorders [Japanese Patent Unexamined Published Application (hereinafter referred to as "J. P. KOKAI" No. Sho 63-54320), a composition for treating patients with alcohol-induced liver disorders (J. P. KOKAI No. Hei 5-213746), therapeutic agent for hepatitis (J. P. KOKAI No. Hei 5-221858), liver regeneration accelerator (J. P. KOKAI No. Hei 5-229940), etc., it has never been known that alanine is useful as a therapeutic agent for primary biliary cirrhosis.

SUMMARY OF THE INVENTION

The object of the present invention is to provide a therapeutic agent for primary biliary cirrhosis, which can be chronically administrated for a long period of time and exhibits an effect superior to that obtained in ordinary medical therapy.

The present invention was completed on the basis of a finding that when L-alanine was administered to terminal cases (stage IV in Scheuer classification) of primary biliary cirrhosis, the symptoms of which had not been improved by the administration of ursodeoxycholic acid, serum total bilirubin which is one of important indexes as factors which exert influences on the prognosis was improved and excellent therapeutic effects were obtained.

Namely, the present invention provides a therapeutic agent for primary biliary cirrhosis, which contains L-alanine or a pharmaceutically acceptable salt thereof as the active ingredient.

DETAILED DESCRIPTION OF THE PREFERRED EMBODIMENTS

Figure 1:
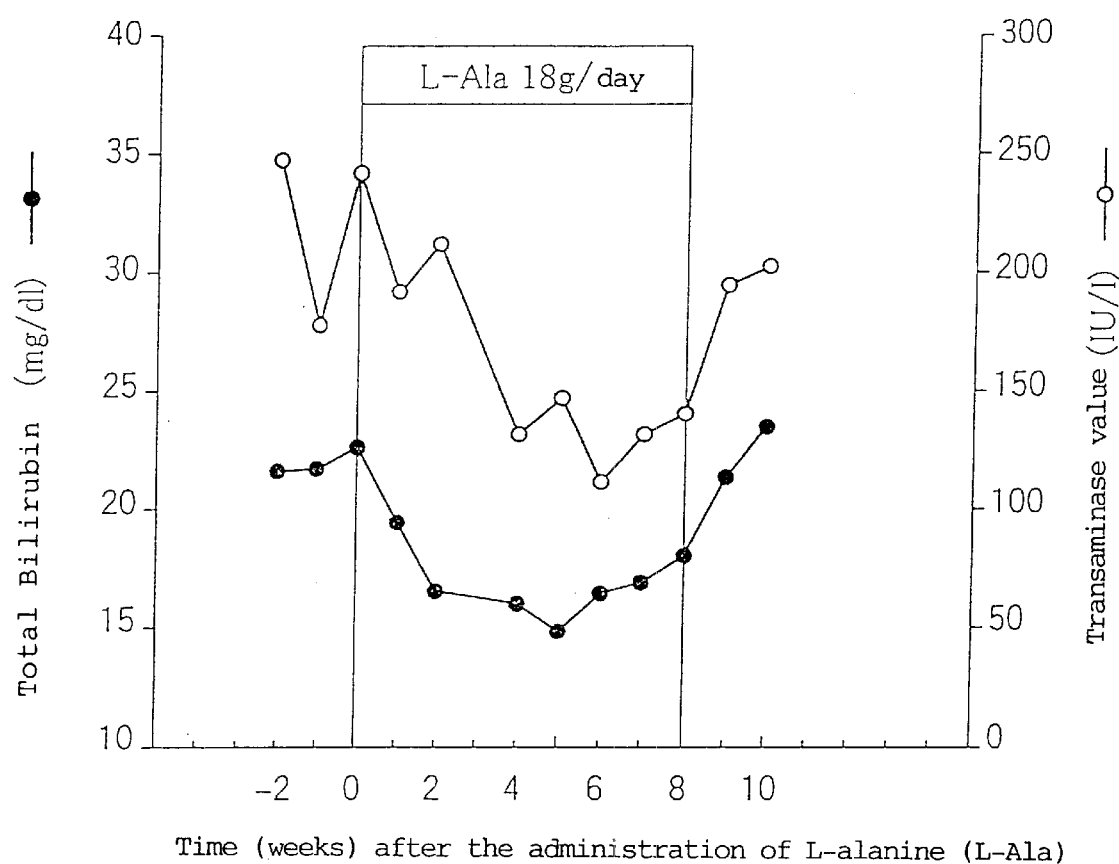
FIG. 1 shows the changes in serum total bilirubin and transaminase value with time after the administration of L-alanine.

L-Alanine used as the active ingredient in the present invention is a non-essential amino acid for mammals, and it is a well-known compound. Pharmaceutically acceptable salts of L-alanine include acid-addition salts and alkali-addition salts thereof. Acids capable of forming pharmaceutically acceptable salts with L-alanine include inorganic acids such as hydrogen chloride, hydrogen bromide, sulfuric acid and phosphoric acid, and organic acids such as acetic acid, lactic acid, citric acid, tartaric acid, maleic acid, fumaric acid and monomethylsulfuric acid. Bases capable of forming pharmaceutically acceptable salts with L-alanine include inorganic bases such as sodium, potassium, calcium and ammonia, and organic bases such as ethylenediamine, propylenediamine, ethanolamine, monoalkylethanolamines, dialkylethanolamines, diethanolamine and triethanolamine.

The therapeutic agent for primary biliary cirrhosis of the present invention can be given by, for example, oral administration or intravenous administration. It is usable in a dosage form suitable for the administration method, such as a form for the internal administration, e. g. a powder, granules, dry syrup (to be taken after suspending it in a suitable amount of water or to be taken as it is like the powder or granules), tablets (including chewable tablets), capsules and a liquid for internal use; or a form for the intravenous injection. Such a preparation can be prepared by using ordinary preparation assistants by an ordinary method. For example, tablets can be prepared by mixing the active ingredient (main ingredient) of the present invention with known assistant substances. The known assistant substances include inert diluents such as lactose, calcium carbonate and calcium phosphate; binders such as gum arabic, corn starch, gelatin, hydroxypropylcellulose and polyvinylpyrrolidone;

coating agents such as hydroxypropylcellulose; bases such as mannitol; excipients such as alginic acid, corn starch and pregelatinized starch; suspending agents such as crystalline cellulose carmellose sodium; corrigents such as sucrose, lactose, aspartame and saccharin; flavors such as peppermint, menthol, lemon oil and cherry; and lubricants such as magnesium stearate and talc.

As for the dosage of the therapeutic agent for primary biliary cirrhosis of the present invention, the dose of the active ingredient for adults is at least 1 g, preferably 5 to 30 g and more preferably 10 to 20 g a day. Because L-alanine is a well-known compound, toxicity data thereof are given in many publications.

The present invention provides the excellent therapeutic agent capable of controlling the symptoms of cases of primary biliary cirrhosis and the advance of the disease.

The following Examples will further illustrate the present invention.

EXAMPLE 1

The clinical effect of L-alanine was examined in a 48 year-old female patient with primary biliary cirrhosis. The patient was suffering from primary biliary cirrhosis in the terminal stages (stage IV in Scheuer classification). After her symptoms had appeared, 600 mg/day of ursodeoxycholic acid was orally administered as a therapeutic agent everyday. However, this treatment became ineffective and the results of biochemical tests also became worse. Under these conditions, 18 g/day of L-alanine was orally administered to the patient in three doses every day for two months. Before and after the administration of L-alanine, two weeks in total of the observation period was taken, and then eight weeks of the administration period was taken. The blood specimen was taken once a week to determine total serum bilirubin and transaminase (AST).

The results are shown in FIG. 1. By the administration of L-alanine, total serum bilirubin and transaminase were reduced. The maximum effect was exhibited two weeks after the start of the administration, and this effect lasted in the course of the administration. As the administration was finished, increase of both total serum bilirubin and transaminase was observed. From the above-described results, the excellent therapeutic effect of L-alanine on the terminal case of primary biliary cirrhosis was confirmed, while the symptoms were not improved by the administration of ursodeoxycholic acid.

Preparation Example 1
Granules (Ingredients and Amount in each Pack)

| Active ingredient: | L-alanine | 6000 mg |
|---|---|---|
| Binder | hydroxypropylcellulose | 100 mg |
| Coating agent | hydroxypropylcellulose | 400 mg |
| Flavor | menthol | very small amount |
| Corrigent | aspartame | suitable amount |

L-alanine as the active ingredient and hydroxypropylcellulose as the binder were weighed and granules were prepared from them by the granule preparation method according to general rules for preparations of The Pharmacopoeia of Japan. The granules were each coated with hydroxypropylcellulose as the coating agent. Then aspartame as the corrigent and menthol as the flavor were added to the coated granules for obtaining good taste and flavor.

Preparation Example 2
Dry syrup

| Active ingredient: | L-alanine | 6000 mg |
|---|---|---|
| Binder | polyvinylpyrrolidone, type 30 | 180 mg |
| Corrigent | aspartame | 90 mg |
| Suspending agent | crystalline cellulose carmellose sodium | 270 mg |
| Flavor | lemon oil | very small amount |

A dry syrup was prepared from the above-described ingredients by an ordinary method.

Preparation Example 3
Chewable Tablets

| Active ingredient: | L-alanine | 1500 mg |
|---|---|---|
| Binder | Polyvinylpyrrolidone, type 30 | 45 mg |
| Corrigent | aspartame | 20 mg |
| Base | mannitol | 500 mg |
| Lubricant | magnesium stearate | suitable amount |
| Flavor | menthol | very small amount |

Chewable tablets were prepared from the above-described ingredients by an ordinary method.

What is claimed:

1. A method of treating primary biliary cirrhosis, which comprises administering an effective amount of L-alanine or a pharmaceutically acceptable salt thereof to a mammal in need of said treatment.

2. The method according to claim 1, wherein said mammal is a human.

3. The method according to claim 2, wherein said effective amount is 5 to 30 g/day.

4. The method according to claim 1, wherein said L-alanine or salt thereof is administered as a composition in a form suitable for oral administration or injection.

5. The method according to claim 4, wherein said form used is suitable for oral administration, which is selected from the group consisting of granules, dry syrup, chewable tablets, powder, capsules and liquid.

6. The method according to claim 1, which reduces total serum bilirubin.

7. The method according to claim 1, which reduces transaminase value.

* * * * *